US007955854B2

(12) United States Patent
Hess et al.

(10) Patent No.: US 7,955,854 B2
(45) Date of Patent: Jun. 7, 2011

(54) ASSESSING HEART FAILURE IN PATIENTS WITH ATRIAL FIBRILLATION USING GDF-15 AND NATRIURETIC PEPTIDES

(75) Inventors: Georg Hess, Mainz (DE); Andrea Horsch, Mannheim (DE); Hendrik Huedig, Penzberg (DE); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/621,560

(22) Filed: Nov. 19, 2009

(65) Prior Publication Data

US 2010/0159608 A1   Jun. 24, 2010

Related U.S. Application Data

(63) Continuation of application No. PCT/EP2008/056261, filed on May 21, 2008.

(30) Foreign Application Priority Data

May 24, 2007   (EP) .................................. 07108852

(51) Int. Cl.
*G01N 33/68* (2006.01)
*G01N 33/48* (2006.01)
(52) U.S. Cl. ............................................ 436/86; 436/63
(58) Field of Classification Search .............. 436/63, 436/86; 422/61, 68.1, 430; 435/29, 810
See application file for complete search history.

(56) References Cited

U.S. PATENT DOCUMENTS 7,655,416 B2 * 2/2010 Hess et al. ...................... 435/7.1

FOREIGN PATENT DOCUMENTS

WO   2008/015254   *   2/2008
WO   2009/027514   *   3/2009

OTHER PUBLICATIONS

Wollert et al. Circulation, vol. 115, Feb. 5, 2007, pp. 962-971.*
Wollert et al. Abstract 2068 in Circulation, vol. 114, 2006, p. 419.*
Kempf et al. Journal of the American College of Cardiology, vol. 50, No. 11, 2007.*
International Search Report issued Sep. 25, 2008 in PCT Application No. PCT/EP2008/056261.
International Preliminary Report on Patentabilty issued Oct. 27, 2009 in PCT Application No. PCT/EP2008/056261.
Beck-Da-Silva, Luis et al., Brain natriuretic peptide predicts successful cardioversion in patients with atrial fibrillation and maintenance of sinus rhythm, Canadian Journal of Cardiology, Oct. 2004, pp. 1245-1248, vol. 20, No. 12.
Kempf, Tibor et al., The Transforming Growth Factor-β Superfamily Member Growth-Differentiation Factor-15 Protects the Heart From Ischemia/Reperfusion Injury, Circulation Research, 2006, pp. 351-360, vol. 98.
Kempf, Tibor et al., Growth Differentiation Factor (GDF)-15 Protects the Heart from Ischemia/Reperfusion Injury in vivo, Supplement to Circulation, Abstracts from Scientific Sessions, Oct. 25, 2005, p. II-281, vol. 122, No. 17.
Tsuchida, Keizo and Tanabe, Kazuhiko, Influence of Paroxysmal Atrial Fibrillation Attach on Brain Natriuretic Peptide Secretion, Journal of Cardiology, Jul. 2004, pp. 1-11, vol. 44, No. 1.
Wollert, Kai C. et al., Prognostic Value of Growth-Differentiation Factor-15 in Patients With Non-ST-Elevation Acute Coronary Syndrome, Circulation, 2007, pp. 962-971, vol. 115, No. 8.

* cited by examiner

*Primary Examiner* — Maureen M Wallenhorst

(57) ABSTRACT

Disclosed are a method, device, and test kit for diagnosing heart failure in a patient exhibiting atrial fibrillation. The method includes determining an amount of growth differentiation factor-15 (GDF -15) in a sample from the patient and comparing the amount of GDF-15 determined with a reference amount of GDF-15, wherein when the amount of GDF-15 determined is greater than the reference amount of GDF-15, a diagnosis of heart failure is indicated.

5 Claims, No Drawings

US 7,955,854 B2

ASSESSING HEART FAILURE IN PATIENTS WITH ATRIAL FIBRILLATION USING GDF-15 AND NATRIURETIC PEPTIDES

RELATED APPLICATIONS

This application is a continuation of PCT/EP2008/056261 filed May 21, 2008 and claims priority to EP 07108852.0 filed May 24, 2007.

FIELD OF THE INVENTION

The present invention is concerned with methods and devices for medical diagnosis. Specifically, it relates to a method of diagnosing heart failure in a subject exhibiting atrial fibrillation, the method comprising determining the amount of GDF-15 in a sample of the subject and comparing the amount of GDF-15 with a suitable reference amount whereby heart failure is to be diagnosed. Moreover, the present invention relates to a diagnostic device and a kit for carrying out the aforementioned method.

BACKGROUND

An aim of modern medicine is to provide personalized or individualized treatment regimens. Those are treatment regimens which take into account a patient's individual needs or risks. Personalized or individual treatment regimens shall be even taken into account for emergency measures where it is required to decide on potential treatment regimens within short periods of time. Heart diseases are the leading cause of morbidity and mortality in the Western hemisphere. The diseases can remain asymptomatic for long periods of time. However, they may have severe consequences once an acute cardiovascular event, such as myocardial infarction, as a cause of the cardiovascular disease occurs.

Heart failure is a condition that can result from any structural or functional cardiac disorder that impairs the ability of the heart to fill with or pump a sufficient amount of blood throughout the body. Even with the best therapy, heart failure is associated with an annual mortality of about 10%.

Heart failure often remains undiagnosed, particularly when the condition is considered "mild". The conventional diagnostic techniques for heart failure are based on the well known vascular volume stress marker NT-proBNP. However, the diagnosis of heart failure under some medical circumstances including atrial fibrillation based on NT-proBNP appears to be incorrect for a significant number of patients but not all (e.g., Beck 2004, Canadian Journal of Cardiology 20: 1245-1248; Tsuchida 2004, Journal of Cardiology, 44:1-11). However, especially patients which suffer from heart failure and which exhibit atrial fibrillation would urgently need—besides medical interventions for the atrial fibrillation—a supportive therapy of the heart failure. On the other hand, as a consequence of an incorrect diagnosis of heart failure, many patients will receive a treatment regimen which is insufficient or which may have even adverse side effects.

Therefore, there is a need for diagnostic measures which allow a reliable and fast diagnosis of heart failure in patients exhibiting atrial fibrillation in order to allow for an efficient medical treatment regimen.

The technical problem underlying the present invention can be seen as the provision of means and methods for complying with the aforementioned needs. The technical problem is solved by the embodiments characterized in the claims and herein below.

SUMMARY OF THE INVENTION

Accordingly, the present invention relates to a method of diagnosing heart failure in a subject exhibiting atrial fibrillation, said method comprising
  (a) determining the amount of GDF-15 in a sample of said subject; and
  (b) comparing the amount of GDF-15 determinant step a) with a suitable reference amount whereby heart failure is to be diagnosed.

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for monitoring, confirmation, and subclassification of a subject. The method may be carried out manually or assisted by automation. Preferably, step (a) and/or (b) may in total or in part be assisted by automation, e.g., by a suitable robotic and sensory equipment for the determination in step (a) or a computer-implemented comparison in step (b).

DETAILED DESCRIPTION OF THE INVENTION

The term "diagnosing" as used herein means assessing as to whether a subject exhibiting atrial fibrillation suffers from heart failure, or not. As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention.

Diagnosing according to the present invention includes monitoring, confirmation, subclassification and prediction of the relevant disease, symptoms or risks therefor. Monitoring relates to keeping track of an already diagnosed disease. Confirmation relates to the strengthening or substantiating a diagnosis already performed using other indicators or markers. Subclassification relates to further defining a diagnosis according to different subclasses of the diagnosed disease, e.g. defining according to mild and severe forms of the disease.

The term "subject" as used herein relates to animals, preferably mammals, and, more preferably, humans. Preferably, the subject referred to in accordance with the aforementioned method suffers from heart failure or exhibits the symptoms or clinical parameters, such as an increased NT-proBNP level, accompanied therewith, i.e. being at least suspect to suffer from heart failure. Moreover, the subject referred to in accordance with the present invention shall also exhibit atrial fibrillation.

"Atrial fibrillation" as used herein refers to an abnormal heart rhythm which involves the two upper chambers of the heart. In a normal heart rhythm, the impulse generated by the sino-atrial node spreads through the heart and causes contraction of the heart muscle and pumping of blood. In AF, the regular electrical impulses of the sino-atrial node are replaced by disorganized, rapid electrical impulses which result in irregular heart beats. Atrial fibrillation may be, preferably, diagnosed on an electrocardiogram. Characteristic findings are, preferably, the absence of P waves, unorganized electrical activity in their place, and irregularity of R—R interval due to irregular conduction of impulses to the ventricles. Irrespective of heart failure, subjects exhibiting atrial fibrillation have increased amounts of the heart failure gold-standard biomarker NT-proBNP in the blood. Accordingly, said subjects can not be reliably diagnosed for heart failure based on NT-proBNP, solely.

However, in a preferred embodiment of the method of the present invention, the method further (i.e. in addition to the determination of GDF-15) comprises the steps of determining the amount of a natriuretic peptide in said sample of the subject and comparing the amount of the natriuretic peptide to a reference. Said further steps may be carried out simultaneously or prior or subsequently to the determination of GDF-15 according to the method of the present invention. More preferably, the natriuretic peptide is initially determined and heart failure will be confirmed as described herein above by a subsequent GDF-15 determination.

The term "natriuretic peptide" comprises Atrial Natriuretic Peptide (ANP)-type and Brain Natriuretic Peptide (BNP)-type peptides and variants thereof having the same predictive potential. Natriuretic peptides according to the present invention comprise ANP-type and BNP-type peptides and variants thereof (see e.g. Bonow, 1996, Circulation 93: 1946-1950). ANP-type peptides comprise pre-proANP, proANP, NT-proANP, and ANP. BNP-type peptides comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP). Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NTproBNP is 120 min longer than that of BNP, which is 20 min (Smith 2000, J Endocrinol. 167: 239-46.). Preanalytics are more robust with NT-proBNP allowing easy transportation of the sample to a central laboratory (Mueller 2004, Clin Chem Lab Med 42: 942-4.). Blood samples can be stored at room temperature for several days or may be mailed or shipped without recovery loss. In contrast, storage of BNP for 48 hours at room temperature or at 4° Celsius leads to a concentration loss of at least 20% (Mueller loc.cit.; Wu 2004, Clin Chem 50: 867-73.). Therefore, depending on the time-course or properties of interest, either measurement of the active or the inactive forms of the natriuretic peptide can be advantageous. The most preferred natriuretic peptides according to the present invention are NT-proBNP or variants thereof. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the polypeptides have NT-proBNP properties. NT-proBNP properties as referred to herein are immunological and/or biological properties. Preferably, the NT-proBNP variants have immunological properties (i.e. epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Invest 230:177-181), Yeo et al. (Yeo 2003, Clinica Chimica Acta 338:107-115). Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide. As discussed above already, a preferred reference amount serving as a threshold may be derived from the ULN. The ULN for a given population of subjects can be determined as specified elsewhere in this description. A preferred threshold (i.e. reference amount) for a natriuretic peptide and, in particular for NT-proBNP, is at least one times, more preferably two to four times the ULN. Preferably, the ULN for NT-proBNP referred to in this context is 125 pg/ml. ULNs for the other natriuretic peptides are known in the art and are, preferably, 40 pg/ml for ANP, 100 pg/ml for BNP and 500 pmol/l for NT-proANP. An amount of a natriuretic peptide larger than the reference amount is, more preferably, additionally indicative for a subject suffering from heart failure.

The term "heart failure" as used herein relates to an impaired systolic and/or diastolic function of the heart. Preferably, heart failure referred to herein is also chronic heart failure. Heart failure can be classified into a functional classification system according to the New York Heart Association (NYHA). Patients of NYHA Class I have no obvious symptoms of cardiovascular disease but already have objective evidence of functional impairment. Physical activity is not limited, and ordinary physical activity does not cause undue fatigue, palpitation, or dyspnea (shortness of breath). Patients of NYHA class II have slight limitation of physical activity. They are comfortable at rest, but ordinary physical activity results in fatigue, palpitation, or dyspnea. Patients of NYHA class III show a marked limitation of physical activity. They are comfortable at rest, but less than ordinary activity causes fatigue, palpitation, or dyspnea. Patients of NYHA class IV are unable to carry out any physical activity without discomfort. They show symptoms of cardiac insufficiency at rest. Heart failure, i.e., an impaired systolic and/or diastolic function of the heart, can be determined also by, for example, echocardiography, angiography, szintigraphy, or magnetic resonance imaging. This functional impairment can be accompanied by symptoms of heart failure as outlined above (NYHA class II-IV), although some patients may present without significant symptoms (NYHA I). Moreover, heart failure is also apparent by a reduced left ventricular ejection fraction (LVEF). More preferably, heart failure as used herein is accompanied by a left ventricular ejection fraction (LVEF) of less than 60%, of 40% to 60% or of less than 40%.

The term "Growth-Differentiation Factor-15" or "GDF-15" relates to a polypeptide being a member of the transforming growth factor (TGF)-β cytokine superfamily. The terms polypeptide, peptide and protein are used interchangeable throughout this specification. GDF-15 was originally cloned as macrophage-inhibitory cytokine-1 and later also identified as placental transforming growth factor-β, placental bone morphogenetic protein, non-steroidal anti-inflammatory drug-activated gene-1, and prostate-derived factor (Bootcov loc cit; Hromas, 1997 Biochim Biophys Acta 1354:40-44; Lawton 1997, Gene 203:17-26; Yokoyama-Kobayashi 1997, J Biochem (Tokyo), 122:622-626; Paralkar 1998, J Biol Chem 273:13760-13767). Similar to other TGF-β-related cytokines, GDF-15 is synthesized as an inactive precursor protein, which undergoes disulfide-linked homodimerization. Upon proteolytic cleavage of the N-terminal pro-peptide, GDF-15 is secreted as a ~28 kDa dimeric protein (Bauskin 2000, Embo J 19:2212-2220). Amino acid sequences for GDF-15 are disclosed in WO99/06445, WO00/70051, WO2005/113585, Bottner 1999, Gene 237: 105-111, Bootcov loc. cit, Tan loc. cit., Baek 2001, Mol Pharmacol 59: 901-908, Hromas loc cit, Paralkar loc cit, Morrish 1996, Placenta 17:431-441 or Yokoyama-Kobayashi loc cit. GDF-15 as used herein encompasses also variants of the aforementioned specific GDF-15 polypeptides. Such variants have at least the same essential biological and immunological properties as the specific GDF-15 polypeptides. In particular, they share the same essential biological and immunological properties if they are detectable by the same specific assays referred to in this specification, e.g., by ELISA assays using polyclonal or monoclonal antibodies specifically recognizing the GDF-15 polypeptides. A preferred assay is described in the accompanying Examples. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific GDF-15 polypeptides. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Moreover, the variants referred to herein include fragments of the specific GDF-15 polypeptides or the aforementioned types of variants as long as these fragments have the essential immunological and biological properties as referred to above. Such fragments may be, e.g., degradation products of the GDF-15 polypeptides. Further included are variants which differ due to post-translational modifications such as phosphorylation or myristylation.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

Determining the amount of the peptides or polypeptides referred to in this specification relates to measuring the amount or concentration, preferably semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal -may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on ELECSYS analyzers), CBA (an enzymatic Cobalt Binding Assay, available for example on Roche-Hitachi analyzers), and latex agglutination assays (available for example on Roche-Hitachi analyzers).

Preferably, determining the amount of a peptide or polypeptide comprises the steps of (a) contacting a cell capable of eliciting a cellular response the intensity of which is indicative of the amount of the peptide or polypeptide with the peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)$_2$ fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable lable prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand: The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethyl-benzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences), ECF (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}S$, $^{125}I$, $^{32}P$, $^{33}P$ and the like. A radioactive label can be detected by any method known and appropriate, e.g. a light-sensitive film or a phosphor imager. Suitable measurement methods according the present invention also include precipitation (particularly immunoprecipitation), electrochemiluminescence (electro -generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the polypeptide or peptide as well as any value or parameter which correlates thereto or can be derived therefrom. Such values or parameters comprise intensity signal values from all specific physical or chemical properties obtained from the peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amount determined in step a) and the reference amount, it is possible to assess whether a subject indeed suffers from heart failure. Therefore, the reference amount is to be chosen so that either a difference or a similarity in the compared amounts allows identifying those subjects which belong into the group of subjects suffering from heart failure.

Accordingly, the term "reference amounts" as used herein refers to amounts of the polypeptides which allows for identifying a subject suffering from heart failure among those exhibiting atrial fibrillation. Accordingly, the reference may either be derived from (i) a subject exhibiting atrial fibrillation which is known to suffer from a heart failure or (ii) a subject exhibiting atrial fibrillation which is known not to suffer from a heart failure. Moreover, the reference amounts, preferably, define thresholds. Suitable reference amounts or threshold amounts may be determined by the method of the present invention from a reference sample to be analyzed together, i.e. simultaneously or subsequently, with the test sample. A preferred reference amount serving as a threshold may be derived from the upper limit of normal (ULN), i.e. the upper limit of the physiological amount to be found in a population of subjects (e.g. patients enrolled for a clinical trial). The ULN for a given population of subjects can be determined by various well known techniques. A suitable technique may be to determine the median of the population for the peptide or polypeptide amounts to be determined in the method of the present invention. The ULN for GDF-15 is within the range of 500 to 650 pg/ml, more preferably, within the range of 550 to 650 pg/ml and, most preferably, 570 pg/ml.

In principle, it has been found that increased amounts of a GDF-15 in a sample of a subject exhibiting atrial fibrillation are indicative for heart failure. Determining GDF-15 as a biomarker for heart failure will, thus, strengthen the diagnosis of heart failure based on NT-proBNP or another natriuretic peptide, in particular, under circumstances where a diagnosis based on the latter peptides has turned out to result in false positives or negatives. Based on said findings and the method of the present invention, hidden heart failure (i.e. heart failure which remains unrecognized because the currently applied diagnostic standards are disregarded, such as in the case of atrial fibrillation) can be treated more efficiently. The method of the present invention, advantageously, allows for a reliable, fast and less cost intensive diagnosis and can be implemented even in portable assays, such as test strips. Therefore, the method is particularly well suited for diagnosing emergency patients. Thanks to the findings of the present invention, a suitable therapy for a subject can be reliably selected, e.g., a therapy for heart failure. Severe side effects caused by the wrong treatment of patients can be avoided.

The present invention, furthermore, relates to a device for diagnosing heart failure in a subject exhibiting atrial fibrillation comprising
 (a) means for determining the amount of GDF-15 in a sample of a subject exhibiting atrial fibrillation; and
 (b) means for comparing the amount determined by the means of a) with a suitable reference amount whereby diagnosis of heart failure is allowed.

The term "device" as used herein relates to a system of means comprising at least the aforementioned means operatively linked to each other as to allow the diagnosis. Preferred means for determining the amount of GDF-15, preferably, in combination with a natriuretic peptide, and means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to obtain the desired results. Preferably, the means are comprised by a single device in such a case. Said device may accordingly include an analyzing unit for the measurement of the amount of the peptides or polypeptides in an applied sample and a computer unit for processing the resulting data for the evaluation. Alternatively, where means such as test strips are used for determining the amount of the peptides or polypeptides, the means for comparison may comprise control strips or tables allocating the determined amount to a reference amount. The test strips are, preferably, coupled to a ligand which specifically binds to the peptides or polypeptides referred to herein. The strip or device, preferably, comprises means for detection of the binding of said peptides or polypeptides to the ligand. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test strips or electronic devices which merely require loading with a sample. The results may be given as output of raw data which need interpretation by the clinician. Preferably, the output of the device is, however, processed, i.e. evaluated, raw data the interpretation of which does not require a clinician. Further preferred devices comprise the analyzing units/devices (e.g., biosensors, arrays, solid supports coupled to ligands specifically recognizing the natriuretic peptide, Plasmon surface resonance devices, NMR spectrometers, mass-spectrometers etc.) or evaluation units/devices referred to above in accordance with the method of the invention.

Finally, the present invention relates to a kit adapted for carrying out the method of the present invention wherein said kit comprises instructions for carrying out the method and
 (a) means for determining the amount of GDF-15 in a sample of a subject exhibiting atrial fibrillation; and
 (b) means for comparing the amount determined by the means of a) with a suitable reference amount allowing diagnosis of heart failure.

The term "kit" as used herein refers to a collection of the aforementioned means, preferably, provided in separately or within a single container. The container, also preferably, comprises instructions for carrying out the method of the present invention. Accordingly, a kit adopted for carrying out the method of the present invention comprises all components required for practicing said method in an ready-to-use manner, e.g., in a premixed form with adjusted concentrations of the components used for determination and/or comparison.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Example 1

Determination of GDF-15 and NT-proBNP in Serum and Plasma Samples

To determine the concentration of GDF-15 in serum and plasma samples, a immunoradiometric assay (IRMA) using a polyclonal, GDF-15 affinity chromatography-purified, goat anti-human GDF-15 IgG antibody from R&D Systems (AF957) was developed. Maxisorp Startubes (Nunc) were coated overnight at 4° C. with 0.5 µg anti-GDF-15 IgG in 0.1 M Na-carbonate buffer (pH 9.0), and then washed t phosphate buffered saline with 0.1% TWEEN 20. Serum or plasma samples (100 µl) were diluted 1:1 with assay buffer (30 g/l BSA, 10 g/l bovine IgG, 1% goat serum, 0.1% Na -azide, 1 M NaCl, 40 mM Na phosphate buffer, pH 7.4), added to the tubes, and incubated for 16 hours at 4° C. After two washing steps, 10 ng of [125I]-iodinated anti-GDF-15 IgG (specific activity 0.74 MBq/µg) were diluted in 200 µl assay buffer, added to each tube, and incubated for 4 hours at room temperature. After three final washing steps, bound radioactivity was quantified in a gamma counter (LKB Wallac 1261). In each experiment, a standard curve was generated with recombinant human GDF-15 from R&D Systems (957-GD/CF). The results with new batches of recombinant GDF-15 protein were tested in standard plasma samples and any deviation above 10% was corrected by introducing an adjustment factor for this assay. GDF -15 measurements in serum and plasma samples from the same patient yielded virtually identical results after correction for eventual dilution factors. The detection limit of the assay was 20 pg/ml. The intra assay coefficient of variation determined for mean GDF-15 levels of 744, 1518, and 8618 pg/ml was 5.6, 5.9, and 6.5%, respectively. The inter-assay coefficient of variation determined for mean GDF-15 levels of 832, 4739, and 9230 pg/ml was 8.6, 5.7, and 4.4%, respectively.

NT-proBNP levels were determined with an immunoassay on an ELECSYS 2010 with a detection limit of 20 pg/ml.

Example 2

The NT-proBNP Levels but not GDF-15 Levels are Influenced by Atrial Fibrillation A total of 273 patients having sinus rhythm when examined by electrocardiography were analyzed for changes in the GDF-15 and NT-proBNP levels. The same analysis was done for a total of 17 patients exhibiting atrial fibrillation. Moreover, the left ventricular ejection fraction was determined.

The plasma levels of GDF-15 and NT-proBNP were determined as described in the example above.

The results of the study are shown in the following table:

| LVEF [%] | GDF-15 [pg/ml] | | NT-proBNP [pg/ml] | |
| --- | --- | --- | --- | --- |
| | Sinus Rhythm (n = 273) | Atrial Fibrillation (n = 17) | Sinus Rhythm (n = 273) | Atrial Fibrillation (n = 17) |
| >60% Median | 609.53 (n = 31) | 620.84 (n = 7) | 127.85 (n = 31) | 1061.0 (n = 7) |
| 40-60% Median | 642.61 | 1054.64 | 384.0 | 1018.00 |

As is evident from the table, GDF-15 is significantly increased in patients having a LVEF of below 60% (i.e., between 40 and 60%) compared to those having an almost physiological LVEF of 60% or more. NT-proBNP is, however not able to discriminate between these patients. It should be noted that the patients having a LVEF between 40 and 60% are most likely to be diagnosed as false positives based on NT-proBNP because other symptoms and clinical signs of heart failure are not or only weakly apparent.

What is claimed is:

1. A method of diagnosing heart failure in a subject exhibiting atrial fibrillation, the method comprising
   determining an amount of growth differentiation factor-15 (GDF-15) in a sample from the subject and
   comparing the amount of GDF-15 determined with a reference amount of GDF-15, wherein when the amount of GDF-15 determined is greater than the reference amount of GDF-15, a diagnosis of heart failure is indicated, wherein the reference amount is derived from a subject exhibiting atrial fibrillation and known to be suffering from heart failure.

2. The method of claim 1 wherein the heart failure is accompanied by a left ventricular ejection fraction (LVEF) of less than 60%.

3. The method of claim 1 wherein the reference amount of GDF-15 is an upper limit of normal (ULN).

4. The method of claim 3 wherein the ULN for GDF-15 is 500 to 650 pg/ml.

5. The method of claim 3 wherein the ULN for GDF-15 is 570 pg/ml.

* * * * *